Figure 1:
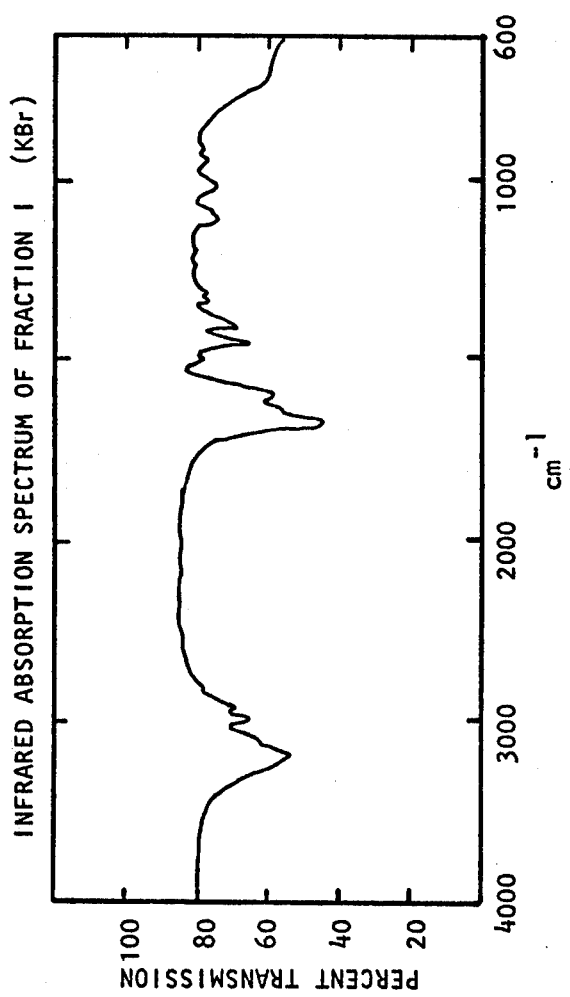

United States Patent [19]

Perlman et al.

[11] 4,025,619

[45] May 24, 1977

[54] BROAD SPECTRUM ANTIBIOTICS

[75] Inventors: David Perlman, Madison, Wis.; Michel Alfred Sylvestre, Ville de Leval, Canada; Takuo Sakai, Osaka, Japan

[73] Assignee: Wisconsin Alumni Research Foundation, Madison, Wis.

[22] Filed: Oct. 17, 1975

[21] Appl. No.: 623,413

[52] U.S. Cl. ............................. 424/115; 195/80 R
[51] Int. Cl.² ........................................ A61K 35/74
[58] Field of Search ................... 424/115; 195/80 R

[56] References Cited

OTHER PUBLICATIONS

Sylvestre et al., J. of Antibiotics, vol. 28, pp. 73–74, Apr. 1975.

*Primary Examiner*—Jerome D. Goldberg
*Attorney, Agent, or Firm*—McDougall, Hersh & Scott

[57] ABSTRACT

Broad spectrum antibiotics derived from the extracellular antibiotic fraction produced by the fermentation of Mycoplasma sp. RP III.

4 Claims, 7 Drawing Figures

BROAD SPECTRUM ANTIBIOTICS

The invention described herein was made in the course of work under a grant or award from the Department of Health, Education, and Welfare.

This invention relates to the field of antibiotics and to new and improved broad spectrum antibiotics.

It is an object of this invention to produce and to provide a method for producing two extracellular antibiotics derived from the growth in a suitable nutrient medium of Mycoplasma sp. RP III.

The new antibiotics, forming the subject matter of this invention, will hereinafter be referred to as Factor I and Factor II in which Factor I has been found to be effective to inhibit Gram-positive and Gram-negative bacteria in vitro including protection of mice from Pseudomonas and Staphyloccoccus infection, and Factor II, identified as a lipid, which has been found to inhibit Gram-positive and Gram-negative bacteria, Candida species, having high cytotoxicity.

As previously reported in Sylvestre, M. and D. Perlman: Antibiotics from Mycoplasma sp. RP III. Characterization of antibiotics produced by Mycoplasma sp. RP III, J. Antibiotics 28:73-74, 1975, three types of antibiotics have been produced from this Mycoplasma sp. RP III originally isolated from rat pituitary cultures: one of which was extracellular, another of which was intracellular, and the third was associated with viable cells. Continued investigation of the antibiotic activities of the extracellular antibiotics produced by the fermentation of Mycoplasma sp. RP III has led to the discovery of extracellular Factor I and Factor II, each of which has been found to inhibit growth of Gram-negative and Gram-positive bacteria and to have other desirable biological properties.

Mycoplasma sp. RP III

A deposit of Mycoplasma sp. RP III is being maintained by American Type Culture Collection at Rockeville Mary., under the ATCC number 31166.

Mycoplasma sp. RP III can be grown in a medium based on Difco PPlo broth (without crystal violet) to which 0.5% by weight yeast extract and 1% by volume calf serum has been added. Aliquots can be stored until needed by freezing at −20° C. To the present, it appears that frequent transfers of the inoculum is required, otherwise the surviving cells lose their ability to produce antibiotics. Best results have been obtained when the culture is incubated 35°-36° C and transferred every 24 hours.

Preparation of Extracellular Antibiotics by Mycoplasma sp. RP III

Culture of Mycoplasma sp. RP III can be maintained on Difco PPLO agar (without crystal violet) supplemented with sterile bovine serum at a level of 1% by volume. Once the culture is established on the agar surface, as on Petri dishes containing 15 ml of medium per 100 mm diameter dish, the plates can be stored at 4° C for up to 6 months. Initial incubation of the plates is at 34°-36° C for up to five days.

Fluid cultures of Mycoplasma sp. RP III can be started from the agar plates by transferring a broth of the agar containing the Mycoplasma colonies to flasks of Difco PPLO broth (without crystal violet) supplemented with 1 g/l of Difco yeast extract and 1% by volume sterile bovein serum. The inoculated flasks (200 ml medium per 250 ml Erlenmeyer flask) are incubated at 35° C for up to four days. During this incubation interval, the cell count increases to about 1 $\times 10^{10}$ colony-forming units per ml. These cells can be used to inoculate fermentation flasks, or aliquots of the culture can be frozen at −20° C to −170° C for future use as inoculum for starting fermentations.

The fermentation medium is composed of Difco PPlo broth (without crystal violet) supplemented with 1% sterile bovine serum and 1.5% by weight Difco yeast extract. The medium is prepared by dissolving the two Difco materials in deionized water, subdividing the solution into Erlenmeyer flasks (500 ml per 2 liter flask or 100 ml per 250 ml flask) and plugging the flasks with cotton. The flasks are then autoclaved at 121° C for 30 minutes and then cooled to room temperature. Sterile bovine serum is then added to give a final concentration of 1% by volume and the pH adjusted with sterile 1 N NaOH to a pH of 7.7 . The flasks of the fermentation medium are then inoculated with aliquots of 24 hour old culture so that inoculum amounts to about 50% of the volume of the fermentation flask. The inoculated flasks are placed on a New Brunswick Scientific Company Gyrotary shaker operating at 400 rpm, with a 1 inch displacement and maintained at a temperature of 35° C. Incubation is continued for four to five days and checks for bacterial contamination are made periodically, as by direct microscopic inspection. At the end of the incubation interval, the replicate flasks of fermented media are pooled.

The composition of Difco PPLO broth* is well known to the skilled in the art such that broths of similar composition from other sources may be used without deviation from the preparation of the extracellular antibiotics from the Mycoplasma sp. RP III as described above.

\* Difco PPLO composition: 50 grams beef heart extract;
10 grams bacto peptone;
5 grams sodium chloride; 6 water to 1 liter.

Optimum antibiotic activity is achieved by the use of a fermentation medium in which a bovine calf serum, in an amount within the range of 0.5 - 4% by volume, and yeast extract in an amount within the range of 0.2 - 2% by weight are added to the Difco PPLO broth (without crystal violet) or other suitable broth. By way of modification of the fermentation in the foregoing examples, addition of amino acids, such as casamino acid, in amounts wihtin the range of 0.1 - 2% by weight, give increased antibiotic production, at least during the early stages of the fermentation period. Best results were secured, when viewed from the standpoint of the fermentation and the yield of antibiotic, by the use of the shaken culture technique described, as compared to static culture for the fermentation phase.

Antibiotic yield is also influenced by pH of the fermentation media, with best results being secured within the pH range of 7.2 to 8.2 and preferably within the range of 7.5 to 8.0 wherein antibiotic activity is increased. For adjustment of the media to the desired pH range, use can be made of alkaline substance material such as sodium hydroxide or other alkali metal hydroxide.

Briefly described, the preparation of extracellular Factor I from the fermentation product comprises the steps of (1) adjusting the pH of the fermentation medium to about 4.5 and heating for a short period of time to a temperarure of 25°-65° C and preferably 50°-60° C above room temperature, treating with charcoal to remove impurities; extraction from aqueous medium with a mixture of ethylacetate-methanol at a pH of about 4.5 and then subjecting the extraction product to chromotographic separation on a cation-exchange resin, followed by elution of the extracellular Factor I with formic acid.

PREPARATION OF FACTOR I

EXAMPLE I

Pooled fermented medium (30 liters), from the fermentation, was adjusted to pH 4.5 with concentrated HCL and heated for 3 minutes in an 80° C water bath. After the material had cooled to room temperature (25°), the formed precipitate was removed by filtration through a Whatman No. 1 filter paper and discarded. Charcoal (Darco G-60, obtained from Fisher Scientific Company) was added to the filtrate to a level of 30 grams per liter and the suspension stirred for one hour at room temperature. 28.5 liters of the filtrate was evaporated in vacuo to 1.4 liters and the concentrate was extracted three times with 1.4 liters of a mixture of ethyl acetate - methanol in the ratio of 9 volumes of ethyl acetate to 1 volume of methanol. The solvent layers were pooled and evaporated to dryness in vacuo.The residue as dissolved in a minimum amount of distilled water (75 ml) and the pH was adjusted to pH 6.5 by mixing with Dowex 1 × 4 resin (OH⁻cycle) in a batchwise manner. The antibiotic containing solution was then applied to a cation exchange resin column ($H^+$cycle) (Amberlite CG-50 from Rohm & Haas, 2.8 × 45 cm) and the antibiotic was eluted, using a 0.2 N formic acid solution. 20 ml fractions were collected and the bioactive fractions (tubes 13-25 ) were pooled to give a volume of 250 ml. This solution was evaporated to dryness in vacuo. The residue was dissolved in a minimum of methanol (50) and sufficient diethylether (50ml) was added to give a 50% mixture and the formed precipitate was removed by centrifugation. The supernatant solution was evaporated to dryness and the residue dissolved in 50 ml of water and rechromatographed on the CG-50 resin ($H^+$cycle, 2.8 × 45 cm). The bioactive material was eluted with 0.2 N formic acid and the bioactive fractions (200 ml) were combined and passed through an ion exchange resin (Dowex 1 × 4 column - OH⁻cycle) to remove excess acid and adjust the pH to 6.5 /The bioactive fractions were then combined and evaporated to dryness in vacuo. The solids were dissolved in a minimum of alcohol (3 ml of methanol) and ethylether was added until the solution became cloudy.The precipitate as removed by filtration and dried in a dessicator. It was then placed in a cold room at 4° C and after 15 days at this temperature, about 1 mg of hygroscopic semi-crystalline solid was obtained. The material, extracellulor Factor I, represented the yield from 30 liters of fermented medium.

CHEMICAL CHARACTERIZATION OF EXTRACELLULAR FACTOR I

Figure 2:
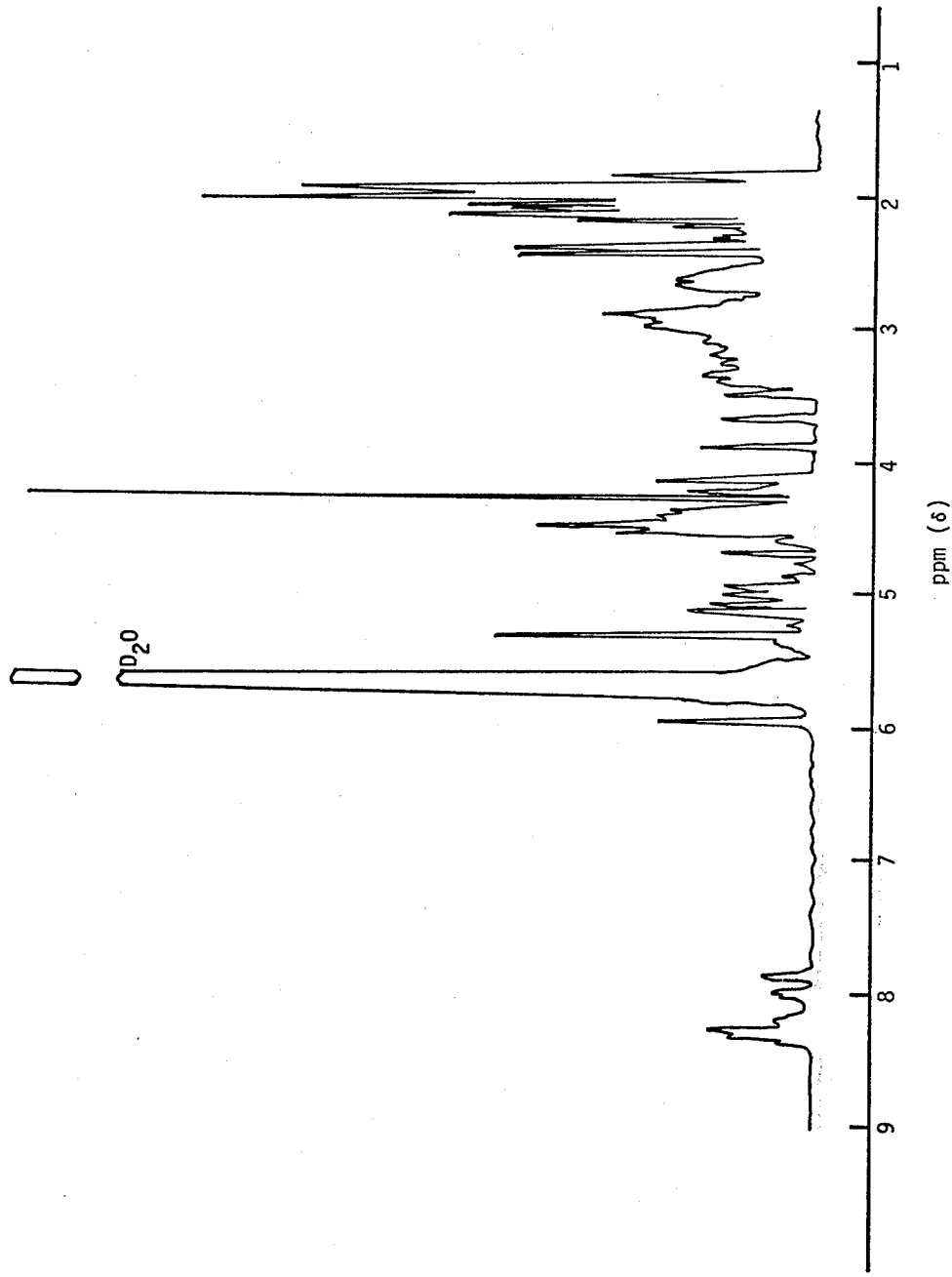

Extracellular Factor I is a basic substance and in paper ionophosersis (Whatman No. 1 paper) moved 3.3 cm towards the cathode at pH 1.9 (acetic acid - formic acid - water in the ratio of 20:2:78 on the volume basis) and 5 volts/cm for 20 minutes (the $R_{alanine}$ was 0.16 ). The melting point was 120° C and it had no significant absorption in the ultra violet. The infrared spectrum (KBr pellet) and the NMR spectrum in deuterium oxide ($D_2O$) are presented in FIGS. 1 and 2.

Antibacterial potency of Factor I was lost when the solutions were stored at alkaline pH, when the material was dissolved in acetone, or when the material was lyophilized. Acidic solutions in water were stable for periods of one month up to 5° C. Spot tests showed positive reactions for the following reagents: $CeSO_4$: $I_2$; triphenyltetrazolium. Negative tests were found with the following reagents: phosphotungstic acid; aniline phthalate; ninhydrin; resorcinol-HC1 ; orcinol; and anthrone.

Mobility of extracellular Factor I in paper chromatography and thin layer chromatographic systems are summarized in Tables 1 and 2.

PREPARATION OF EXTRACELLULAR FACTOR II

Briefly described, preparation of Extracellular Factor II from the resulting fermentation medium follows the procedure for preparation of Extracellular Factor I to the completion of the adjustment to a pH of about 4.5 and heating to above ambient temperature for a few minutes. Thereafter, the product is adjusted to a pH of about 3 and extracted, as with ethylether and then subjecting the extract to chromatographic separation on silica gel.

EXAMPLE II

Pooled fermented medium (30 liters) from the previous fermentation of Mycoplasma sp. RP III was adjusted to pH4.5 with concentrated HCL and heated for 3 minutes in a water bath at 80° C. After the sample had cooled to room temperature (25° C), the formed precipitate was removed by filtration and discarded. Charcoal (Darco G-60) was added to the filtrate at a level of 30 grams per liter and the suspension was stirred for one hour at room temperature.The charcoal was removed by filtration and discarded. The remaining 28.5 liters of filtrate was evaporated in vacuo to 1.4 liters and the concentrate was extracted three times with 1.4 liters of a mixture of 9 volumes ethyl acetate to one volume of methanol.

Extracellular Factor II, an acidic antibiotic, was recovered from the aqueous phase by adjusting the solution to a pH of 3.0 with HC1 and extracting it three times with an equal volume of ethyleter. The ether extracts were combined and evaporated in vacuo. The residue was dissolved in a minimum of ethylether and further purified by preparative thin layer chromatography with silica gel as support, and the following solvent system: $CHCl_3$ -acetone (1:1 by volume); $CHCl_3$ -methyl alcohol (4:1 by volume); and $CHCl_3$ -ethyl acetate (1:1 by volume). The antibiotic containing areas of the silica gel chromatograms were eluted with $CHCl_3$ and the eluates concentrated to a small volume in vacuo. The material, recovered as an oil, amounted to approximately 10 mg per liter of fermented media containing about 10% Extracellular Factor II.

CHEMICAL CHARACTERIZATION

Extracellular Factor II was found to be stable at acid pH but labile at alkaline pH (pH 8). Spot tests show positive reactions for the following reagents: $CeSO_2$: $I_2$ ; phosphotungstic acid; triphenyltetrazolium. Negative reactions were obtained with the following reagents: aniline phthalate; ninhydrin; resorcinol-HCl; orcinol; and anthrone. The mobilities of Factor II in paper chromatographic and in thin layer chromatography are summarized in the following Tables 1 and 2.

Table 1

Mobility of Mycoplasma sp. RP III antibiotics in Paper Partition Chromatography

| solvent system | $R_f$ noted* | |
|---|---|---|
| | Factor I | Factor II |
| water saturated n-BuOH | 0.06 | n.d.** |
| $NH_4Cl$, 3% (w/v) | 0.56 | n.d. |
| n-BuOH-MeOH-$H_2O$ (4:1:2) | 0.44 | n.d. |
| water | 0.53 | n.d. |
| Benzene-MeOH (4:1) | 0.02 | 0.63 |

*Position of antibiotic on paper chromatograms detected by bioautography using *Pseudomonas convexa* in test organism.
**Antibiotic could not be detected and we concluded it was inactivated by the solvent system.

Table 2

Mobility of Mycoplasma sp. RP III Antiobiotics in Thin Layer Chromatography on Silica Gel

| solvent system | $R_f$ noted* | |
|---|---|---|
| | Factor I | Factor II |
| $CHCl_3$-MeOH (8:2) | 0.44 | 0.88 |
| $CHCl_3$-MeOH (1:1) | 0.49 | 0.25 |
| $CHCl_3$-Acetone (8:2) | inactivated | 0.81 |
| $CHCl_3$-Acetone (1:1) | inactivated | 0.42 |
| $CHCl_3$-n-Hexane (2:1) | 0 | 0.31 |
| $CHCl_3$-Benzene (2:1) | 0 | 0.47 |
| EtOAc-AcOH-$H_2O$ (6:2:1) | 0.52 | — |

*Position of antibiotics in thin layer chromatograms was detected by bioautography using *Pseudomonas convexa* as test organism.

BIOLOGICAL CHARACTERISTICS OF FACTORS I AND II

The antimicrobial spectra of Factors I and II are summarized in the following Table 3 which also contains information for comparison with the activities of erythromycin, tetracycline, kanamycin, and gentamicin (complex) against the test organisms.

Cytotoxicity tests, using the inhibition of growth of KB cells (according to the protocols of the National Cancer Institute) showed that purified Factor I had an $ID_{50}$ of 8 mcg/ml and Factor II had an $ID_{50}$ of 5.7 ng/ml. Thus the cytotoxicity of Factor I was about the same as tetracycline or chloramphenicol, while that of Factor II is of the order of the actinomycins in this test system.

In vivo tests using Pseudomonas aeruginosa and Staphylococcus aureus (Gray) as test organisms in mice showed that when crude Extracellular Factor I (previously prepared) was injected subcutaneously at 600 mg/kg, two of the three mice with such injection survived while those not receiving the antibiotic died Antibiotic activity of the fermented medium was determined by adjusting the fermented medium to pH 4.0 with HCl. The acidified solution was heated to 80° C for 3 minutes. The samples were centrifuged and 5 ml of the supernatant solution were neutralized to pH 6.5 with sodium hydroxide and then lyophilized. The recovered solids were dissolved in 0.25 ml of water. The concentrates were assayed for antibiotic activity using an agar diffusion assay with 24 hour old cells of *Pseudomonas convexa* NRRL B-21 in 10 ml of Difco assay medium in a 100 mm Petri dish with 8 mm wells in the agar serving as reservoirs. Incubation was at 26° C for 18 hours and kanamycin solution served as internal standard in the assay plate.

Antimicrobial spectrum of the antibiotic spectra Extracellular Factor I and Factor II were determined by growing the test organisms listed in Table 3 in nutrient broth (except for the Candida cultures which were grown in Sabouraud's medium) for 24 hours and the cells used to inoculate Difco assay agar No. 1 paper discs (6.25 mm) were used as reservoirs. The zones of inhibition were measured after 18 hours at 37° C.

Analytical and preparative thin layer chromatography was carried out using precoated plates (0.25 mm

Table 3

Comparison of Antibiotic Activity of Preparations from Mycoplasma sp. RP III with Other Antibiotics

| assay organisms | diameter of inhibition zone, mm* | | | | | |
|---|---|---|---|---|---|---|
| | Mycoplasma sp. | | erythro-mycin | tetra-cycline | kana-mycin | genta-micin |
| | Factor I | Factor II | | | | |
| *Bacillus subtilis* Marburg | 22 | 24.5 | 26 | 16 | 22 | 24 |
| *Bacillus cereus* ATCC 14579 | 26 | 25 | 25.5 | 23 | 19 | 19 |
| *Staphylococcus aureus* 209P | 14.5 | 25 | 10 | 10 | 19 | 18 |
| *Sarcina lutea* | 16.5 | 20 | 26 | 16 | 15.5 | 10 |
| *Corynebacterium sepedonicum* ATCC 15391 | 17 | 26 | 14 | 13.5 | 22 | 21.5 |
| *Escherichia coli* B | 20.5 | 20 | 13 | 15 | 15 | 24.5 |
| *Erwinia carotovora* ATCC 495 | 24 | 23 | n.z. | 16 | 21 | 22 |
| *Pseudomonas putida* ATCC 21812 | 22 | >40 | n.z. | 9 | 20 | 21 |
| *Pseudomonas convexa* NRRL B-21 | 17 | 31 | — | — | — | — |
| *Pseudomonas aeruginosa* DIFO 3856 | 25 | 26 | — | 28 | 26.5 | 26.5 |
| *Pseudomonas chlororaphis* NRRL B-502 | 25 | 32 | n.z. | tr | 15 | 10 |
| *Pseudomonas syringae* NRRL B-865 | 21 | 29 | tr | 21.5 | 27 | 25.5 |
| *Pseudomonas stutzeri* NRRL B-927 | 22 | >30 | 12.5 | 13.5 | 18.5 | 17 |
| *Pseudomonas aureofaciens* NRRL B-1543P | 20 | 27.5 | n.z. | tr | 14 | 11 |
| *Candida utilis* Y-421 | n.z. | 17.5 | n.z. | n.z. | n.z. | n.z. |
| *Candida albicans* &-4244 | n.z. | 14 | n.z. | n.z. | n.z. | n.z. |

*notes: 6.25 mm paper discs used; discs with Factor I contained 200 mcg; discs with Factor II contained 20 mcg/disc; discs with erythromycin, kanamycin, and gentamicin all contained 5 mcg/disc.

silicia gel layer) obtained from Macheray-Nagel Company.

It will be seen from the results tabulated in Table 3 that Factor I exhibits antibiotic activity in all instances comparable to that of others of the tetracyclines and the other antibiotics, with greater activity being demonstrated against *Bacillus cereus, Staphylococcus aureus, Erwinia carotovora, Pseudomonas chlororaphis, Pseudomonas stutzeri* and *Pseudomonas aureofaciens*, with activity only for Factor I against *Pseudomonas convexa* and *Pseudomonas aureofaciens*. Factor II exhibits antibiotic activity similar to that of tetracycline and the other antibiotics listed in Table 3 with even greater activity being demonstrated against *Staphylococcus auresu, Corynebacterium sepdeonicum, Erwinia carotovora, Pseudomonas putida, Psendomonas syringae* and *Pseudomonas stutzeri*, while activity only for Factor II was demonstrated against *Pseudomonas putida, Pseudomonas convexa, Pseudomonas aureofaciens, Candida utilis* and *Candida albicans*.

It will be apparent from the foregoing that we have provided a balance of broad spectrum antibiotics of considerable utility and that changes may be made in the details of formulation and preparation without departing from the spirit of the invention, especially as defined in the following claims.

We claim
1. A process for the preparation of a broad spectrum extracellular antibiotic (Factor I) comprising cultivating Mycoplasma sp. RP III ATCC 31166 in nutrient medium until a sufficient amount of antibiotic has been produced, adjusting the pH of the fermentation medium to a pH of about 4.5 , heating the medium for a short period of time to a temperature within the range of 25°–65° C, and then extracting an antibiotic at a pH of about 4.5.

2. A broad spectrum extracellular antibiotic (Factor I) produced by the process of claim 1.

3. A process for the preparation of a broad spectrum extracellular antibiotic (Factor II) comprising cultivating Mycoplasma sp. RP III ATCC 31166 in nutrient medium until a sufficient amount of antibiotic has been produced, adjusting the pH of the fermentation medium to a pH of about 4.5 , heating the medium for a short period of time to a temperature within the range of 25°–65° C, and extracting the antibiotic at a pH of about 3.0 .

4. A broad spectrum extracellular antibiotic (Factor II) produced by the process of claim 3.

* * * * *